United States Patent [19]
Chou et al.

[11] Patent Number: 6,111,638
[45] Date of Patent: Aug. 29, 2000

[54] METHOD AND APPARATUS FOR INSPECTION OF A SOLAR CELL BY USE OF A ROTATING ILLUMINATION SOURCE

[75] Inventors: Mau-Song Chou; Richard A. Chodzko, both of Rancho Palos Verdes, Calif.

[73] Assignee: TRW Inc., Redondo Beach, Calif.

[21] Appl. No.: 09/138,169

[22] Filed: Aug. 21, 1998

[51] Int. Cl.$^7$ ................................................ G01N 21/00
[52] U.S. Cl. ................................ 356/239.2; 356/237.2
[58] Field of Search .......................... 356/237.1, 237.2, 356/237.3, 239.1, 239.2, 239.7, 239.8, 371

[56] References Cited

U.S. PATENT DOCUMENTS

| | | | |
|---|---|---|---|
| 4,747,684 | 5/1988 | Weiser | 356/31 |
| 4,989,973 | 2/1991 | Noso et al. | 356/239.8 |
| 5,298,963 | 3/1994 | Moriya et al. | 356/237.2 |
| 5,334,844 | 8/1994 | Pollard . | |
| 5,367,174 | 11/1994 | Bazile | 356/237.6 |
| 5,430,538 | 7/1995 | Kobayashi . | |

FOREIGN PATENT DOCUMENTS

| | | |
|---|---|---|
| 2641866 | 7/1990 | France . |
| 4123916 | 1/1992 | Germany . |

Primary Examiner—Richard A. Rosenberger
Attorney, Agent, or Firm—Michael S. Yatsko; Connie M. Thousand

[57] ABSTRACT

A method and apparatus for inspection of a substrate and a cover glass covering the substrate provides consistent detection of defects in the substrate such as cracks and cracks in the cover glass free of visual inspection of the substrate and the cover glass. An electromagnetic radiating source produces infrared radiation which illuminates the substrate and cover glass at a predetermined azimuth angle. The azimuth angle is varied such that the substrate and cover glass are illuminated at a plurality of azimuth angles. The substrate and the cover glass reflect portions of the incident electromagnetic radiation. A radiation detector collects portions of the reflected radiation and creates a plurality of images therefrom which include indicia representative of the defect in the substrate and the crack in the cover glass.

12 Claims, 5 Drawing Sheets

METHOD AND APPARATUS FOR INSPECTION OF A SOLAR CELL BY USE OF A ROTATING ILLUMINATION SOURCE

BACKGROUND OF THE INVENTION

The present invention relates generally to inspection devices, and more particularly to a device which can perform inspections of substrates and cover glass on a substrate using a dark-field imaging technique.

Cracks in a substrate or in the cover glass over a substrate can result in substrate failures or failures in the system in which the substrate is placed. In particular, when the substrate is a solar cell, a crack in either the solar cell or the cover glass over the solar cell has the potential to severely limit the power output of the solar panel which contains the crack. Whereas a minor crack in the cover glass can usually be repaired, for example by patching with sealants or adhesives, solar cell cracks cannot usually be repaired. In most cases, the solar cell having a crack is removed and is replaced with a new solar cell. It is therefore important to detect cracks in both the substrate and the cover glass and to differentiate cracks in the solar cell from cracks in the cover glass, especially if the crack in the cover glass occur in approximately the same vicinity as a crack in the solar cell thereby obscuring the crack in the solar cell. The current techniques for inspection of solar cells cannot reliably detect both cell cracks and glass cracks simultaneously, nor the coincident cracks.

Current techniques used to detect cracks in cover glass on a substrate such as a solar cell involves a visual inspection. An inspector illuminates the cover glass and the solar cell with properly controlled lighting and physically examines the cover glass with a magnifier looking for defects and cracks. This technique requires the inspector to turn his head around at many different angles to thoroughly inspect the substrate. This physical inspection technique is a time-consuming procedure which can cause fatigue of the inspector's eyes and defects being overlooked due to human error.

What is needed therefore is an apparatus and method for detecting cracks in a substrate and in particular, cracks in a solar cell and the cover glass over the solar cell, and also differentiate between cracks in a solar cell and cracks in the cover glass over the solar cell which provides consistent detection and differentiation of cracks but does not require manual inspection.

SUMMARY OF THE INVENTION

The preceding and other shortcomings of the prior art are addressed and overcome by the present invention which provides an apparatus and a method for detecting cracks in a substrate and cracks in cover glass over a substrate. The apparatus includes an electromagnetic radiating source spaced from the substrate and positioned to illuminate the substrate with electromagnetic radiation. Means are provided to vary the azimuth angle such that the electromagnetic radiation source illuminates the substrate at a plurality of azimuth angles. The substrate reflects portions of the electromagnetic radiation. An electromagnetic radiation detector collects portions of the reflected electromagnetic radiation and creates a plurality of images from the collected radiation in which the images contain indicia representative of the crack.

In a second aspect, the present invention provides a method for detecting cracks in a substrate and in a cover glass over the substrate, such as a solar cell covered by a cover glass, including the steps of illuminating the cover glass and the substrate with electromagnetic radiation at a plurality of azimuth angles, collecting portions of the electromagnetic radiation reflected from the cover glass and substrate, producing a plurality of images from the reflected electromagnetic radiation, and examining the images for indicia of the crack.

The foregoing and additional features and advantage of this invention will become apparent from the detailed description and accompanying drawing figures below. In the figures and the written description, numerals indicate the various features of the invention, like numerals referring to like features throughout for both the drawing figures and the written description.

BRIEF DESCRIPTION OF THE DRAWINGS

Reference is now made to the detailed description of the preferred embodiments, illustrated in the accompanying drawings, in which.

DETAILED DESCRIPTION OF THE PREFERRED EMBODIMENTS

Figure 1:
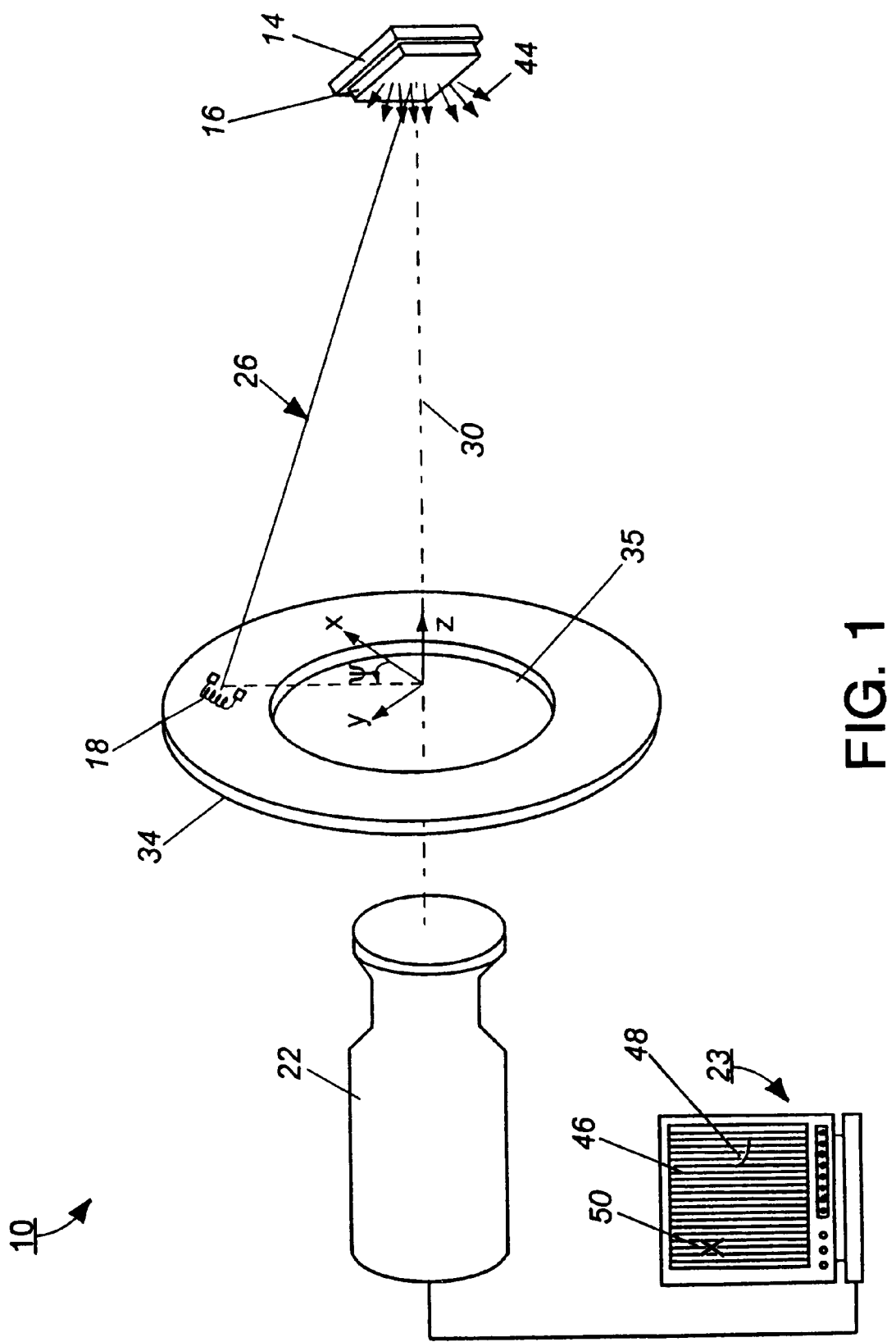
FIG. 1 is an isometric view of the inspection device in accordance with one embodiment of the present invention.

Referring to FIG. 1, an inspection device 10 for inspecting substrates 14, inspecting cover glass 16 over the substrate 14, detecting cracks in the substrate 14, detecting cracks in the cover glass 16, and differentiating between cracks in the substrate 14 and cracks in the cover glass 16 is illustrated. The inspection device 10 can be used to inspect substrates 14 made of materials such as glass, silicon, gallium arsinide, germanium and other substrates used in integrated circuits or energy collecting devices and can also be used to inspect cover glass 16 covering the substrate 14. The present invention is particularly effective when used to detect cracks in a cover glass 16 which covers a solar cells 14 and to differentiate between cracks in the cover glass 16 and cracks in the solar cell 14. The present invention is also useful in detecting a defect, such as a delamination type defect, in a substrate 14.

As illustrated in FIG. 1, the inspection device 10 includes an electromagnetic radiating source 18, an electromagnetic radiation detector 22 such as a video camera 22, means to vary the azimuth angle $\Psi$ at which the substrate 14 and cover glass 16 are illuminated, and, means such as a video monitor 23 to create and display a plurality of images as the azimuth angle $\Psi$ is varied. The electromagnetic radiating source 18 emits electromagnetic radiation 26 which is utilized to illuminate the substrate 14 and cover glass 16 at varying azimuth angles $\Psi$. The electromagnetic radiating source 18 is preferably a spirally wound heater coil 18 which emits electromagnetic radiation 26 having an infrared wavelength. Alternatively, the radiating source 18 can be tungsten halogen lamp, light emitting diode (LED), diode laser or the like, and, the electromagnetic radiation 26 can be of any wavelength between ultraviolet and infrared wavelengths but, it is preferred that the electromagnetic radiation 26 be infrared radiation.

To illuminate the substrate 14 and cover glass 16 at varying azimuth angles Ψ, either the substrate 14 and cover glass 16 or the radiating source 18 is rotated about the centerline 30. If the substrate 14 and cover glass 16 are mounted on a large solar panel, it is preferred that the radiating source 18 be rotated. To do so, the radiating source 18 is attached to a rotatable support structure 34 having an opening 35. The rotatable support structure 34 is preferably rotated about the center line 30 and is positioned such that the radiation detector 22 can view the substrate 14 and cover glass 16 through the opening 35 in the support structure 34.

Figure 2:
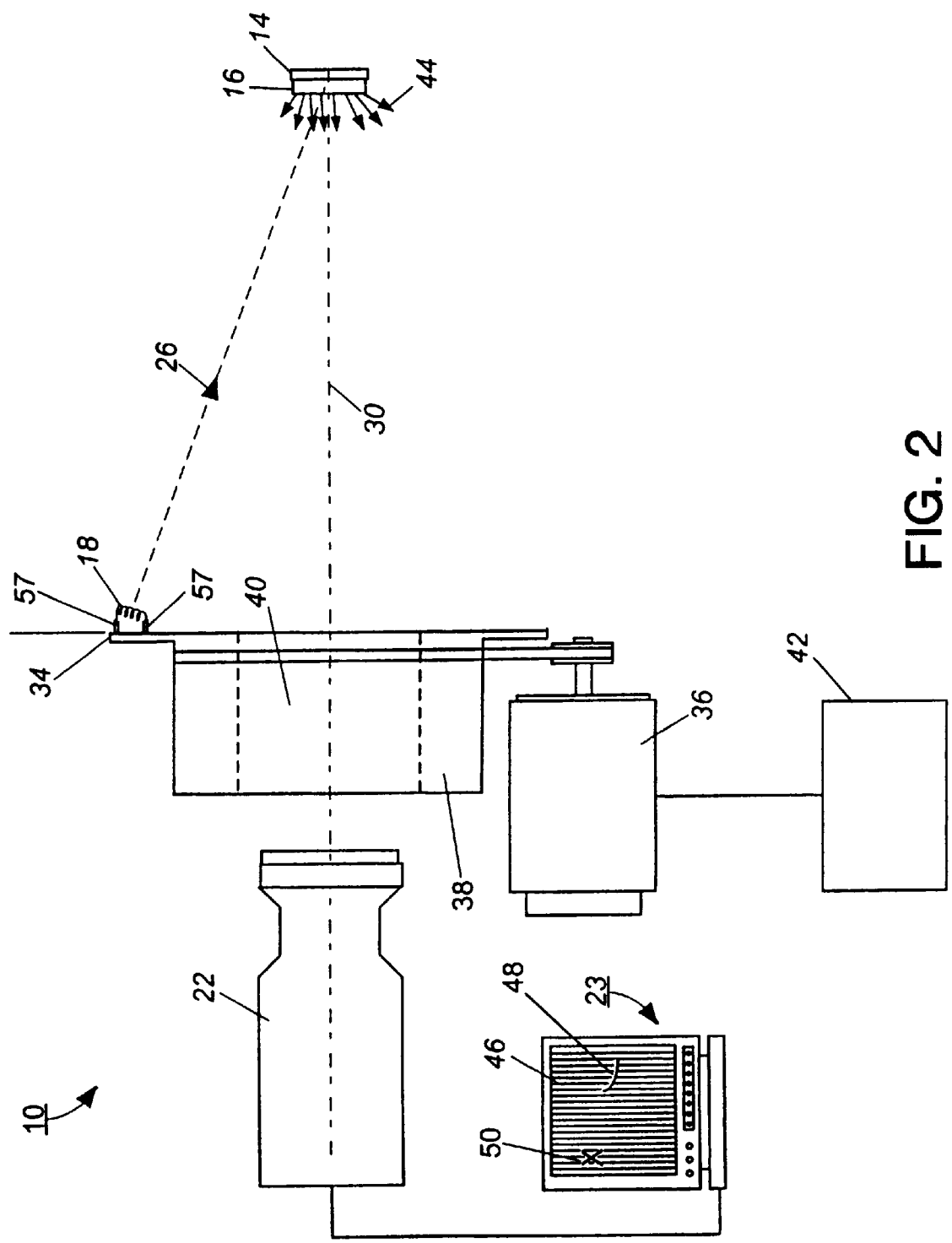
FIG. 2 is a side view of the inspection device in accordance with a second embodiment of the present invention.

Referring to FIG. 2, it is preferred that the rotatable support structure 34 be rotated mechanically with a motor 36 and a slip ring 38 coupled to the support structure 34. Power is supplied from a power source (not shown) to the slip ring 38 which is equipped with metal brushes (not shown) to facilitate transfer of power to the radiating source 18 as the support structure 34 is rotated by the motor 36. An opening 40 is provided in the slip ring 38 and the detector 22 is positioned to view the cover glass 16 and substrate 14 through the opening 40. A speed control unit 42 is coupled to the motor 36 and is used to control the speed of the motor 36 such that the images are displayed on the monitor 23 at a rate which the human eye can monitor. Alternatively, the support structure 34 is rotated manually and batteries (not shown) are attached directly to the support structure 34 to provide power to the radiating source 18.

Referring back to FIG. 1, for the preferred embodiment of the invention, shielding is provided between the radiating source 18 and the detector 22 to shield the detector 22 from direct radiation from the radiating source 18. The shielding can be provided by a separate device (not shown) but it is preferred that the shielding be provided by the support structure 34. For the embodiment of the invention shown in FIG. 2, the slip ring 38 along with the support structure 34 provide shielding between the radiating source 18 and the detector 22.

Referring back to FIG. 1, the substrate 14 and cover glass 16 reflect portions 44 of the incident electromagnetic radiation 26. The detector 22 continually collects a portion of the reflected electromagnetic radiation 44 and creates images which are displayed on a monitor 23 so that a human eye can inspect the images for indicia of a defect in the substrate 14 or a crack in the cover glass 16. The detector 22 can be any device which detects electromagnetic radiation, but, for the preferred embodiment of the invention, the detector 22 is a video camera 22 which is located on the centerline 30 and approximately normal to the surface of the cover glass 16 so that a substantial amount of the surface area of the substrate 14 and cover glass 16 can be focused on within the field of view of the camera 22. The camera 22 continually collects portions of the reflected electromagnetic radiation 44 and produces a plurality of images as the azimuth angle Ψ at which the substrate 14 and cover glass 16 is illuminated is varied. If the substrate 14 and cover glass 16 is perfectly smooth and free of defects, the images will be uniform in appearance, except for the presence of a grid structure 46 if the substrate 14 is a solar cell 14, and, the image will remain uniform in appearance at all azimuth angles Ψ of illumination.

If the cover glass 14 includes a crack, the image will include indicia of the crack 48 when the crack is illuminated at the proper azimuth angle Ψ. Discontinuities in the refractive index of a crack is at a maximum when the crack is illuminated at an azimuth angle Ψ which differs from the azimuth angle Ψ of the glass crack by 90 degrees which will result in maximum reflected radiation 44. On the other hand, discontinuities in the refractive index of a crack is at a minimum when the crack is illuminated along the crack. Hence, as the azimuth angle Ψ is varied, the image of a glass crack 48 will be appear bright momentarily and then darken depending upon the orientation of the azimuth angle Ψ of the illuminating source 18 relative to that of the glass crack. All glass cracks, including straight and curved cracks, can thus be detected when the radiating source 18 completes a 180 degree rotation in azimuth angle Ψ.

If the substrate 14 includes a crack or a defect, the image will include indicia of the crack or defect 50 when the crack or defect is illuminated from any azimuth angle Ψ of illumination. This indicia 50 appears as a dark image on the monitor 23. Although the amount of reflected radiation and thus the intensity of the image produced from glass cracks 48 is dependant on the azimuth angle Ψ of illumination, the dark images of a substrate defect or crack 50 are essentially independent of the azimuth angle Ψ of illumination. As the azimuth angle Ψ is varied, the intensity of the image of a glass crack 48 will fade and brighten intermittently with changes in the azimuth angle Ψ of illumination whereas the dark image of a substrate crack 50 will remain unchanged. In this way, a substrate crack 50 can be detected and differentiated from a glass crack 48 and, in particular, a substrate crack hidden under a glass crack can be detected and differentiated from a glass crack in the cover glass 16 over a substrate 14.

Figure 3:
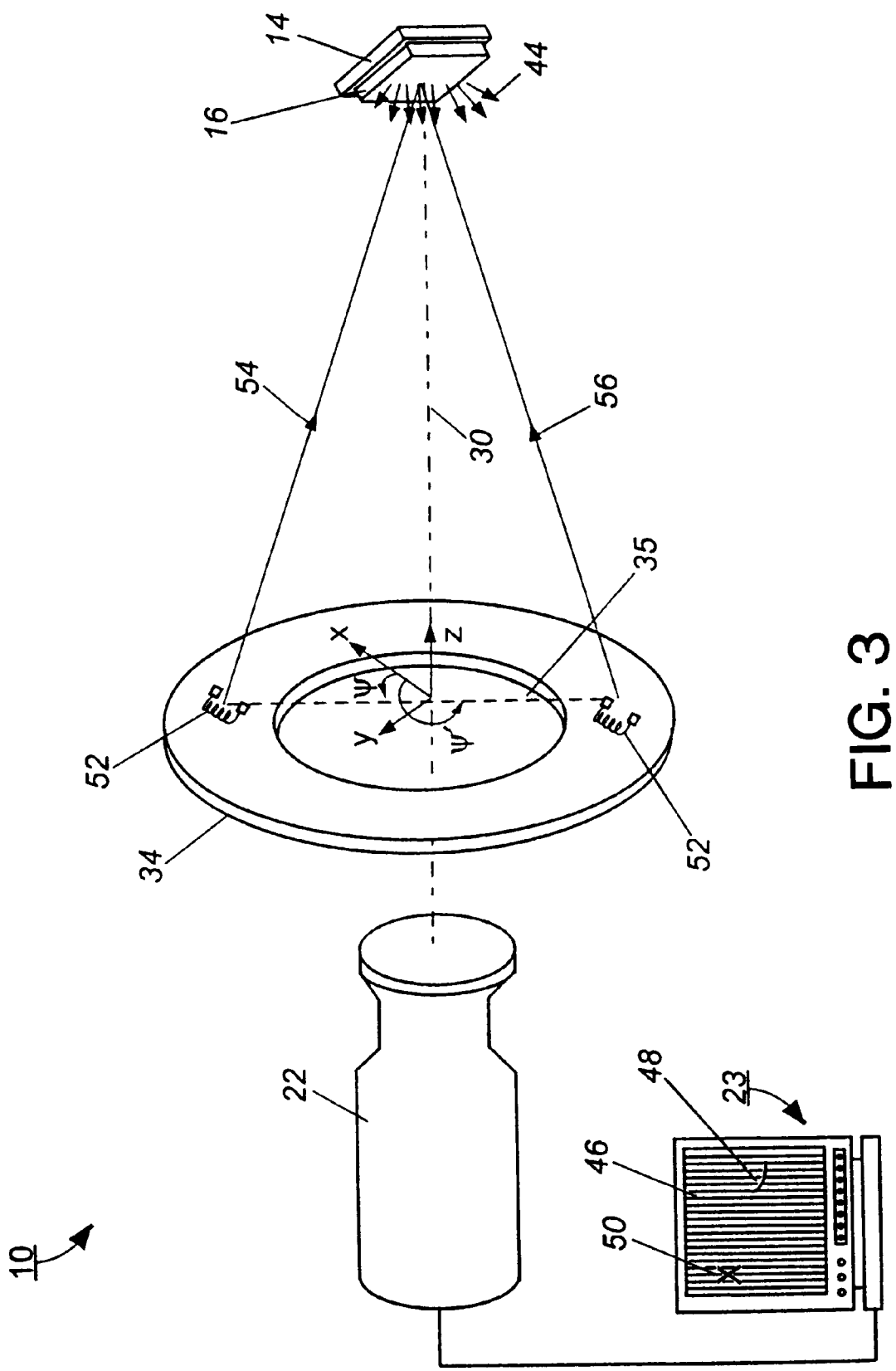
FIG. 3 is an isometric view of the inspection device in accordance with a third embodiment of the present invention.

Referring to FIG. 3 for the preferred embodiment of the invention, the radiating source 18 (FIG. 1) is comprised of two radiating elements 52 which are positioned on the rotatable support structure 34 at opposite sides of the centerline 30 and approximately 180 degrees apart in azimuth angle Ψ from each other. The radiating elements 52 are used to illuminate the substrate 14 and cover glass 16 with radiation rays 54 & 56 from opposite sides at azimuth angles Ψ and Ψ'. The radiation rays 54 & 56 preferably have approximately the same intensity and Ψ' is preferably approximately equal to Ψ+180 degrees. The radiation rays 54 & 56 can simultaneously illuminate the front of the substrate 14 and cover glass 16 from opposite sides such that both rays 54 & 56 can be simultaneously incident normal or along the glass crack depending on the location of the rotatable support structure 34. This results in a higher intensity and more uniform illumination of the substrate 14 and cover glass 16 and in-phase collection of reflected radiation 44 which enhances detection of a glass crack when compared to non-uniform illumination of the substrate 14 and cover glass 16 as is provided by the single radiating source embodiment shown in FIG. 1.

For the preferred embodiment of the invention, the two radiating elements 52 are each spirally wound heater coils, each coil 52 comprised of small diameter heater wire having an approximately 0.38 mm diameter of a material such as nickel/chromium, which is spirally coiled and provided with power from a source (not shown) to create radiating rays 54 & 56. Alternatively, the radiating elements 52 can be tungsten halogen lamps, LEDs, diode lasers or the like. Each radiating element 52 is preferably attached to the support structure 34 with two insulator standoffs 57 and positioned to illuminate the substrate 14 and cover glass 16. For good detection of the reflected radiation 44, it is preferred that the detector 22 have a spectral response that matches the spectral outputs of the radiating elements 52. One such detector 22 for use with the heater coil radiating elements 52 described above, is a platinum-silicide infrared camera 22 known as an Infracam™ made by Inframatrics Inc., located in North Billerica, Mass. which has a spectral response from a wavelength of 1 to 5 microns. For alternative embodiments of the invention in which tungsten halogen lamps, light emitting diodes (LEDs), diode lasers or the like are used as the radiating elements 52, it is preferred that the detector 22 be a silicon photodiode detector, a germanium photodiode detector, an InGaAs photodiode detector or the like such that the spectral outputs of the radiating elements 52 closely matches that of the detector 22.

Figure 4:
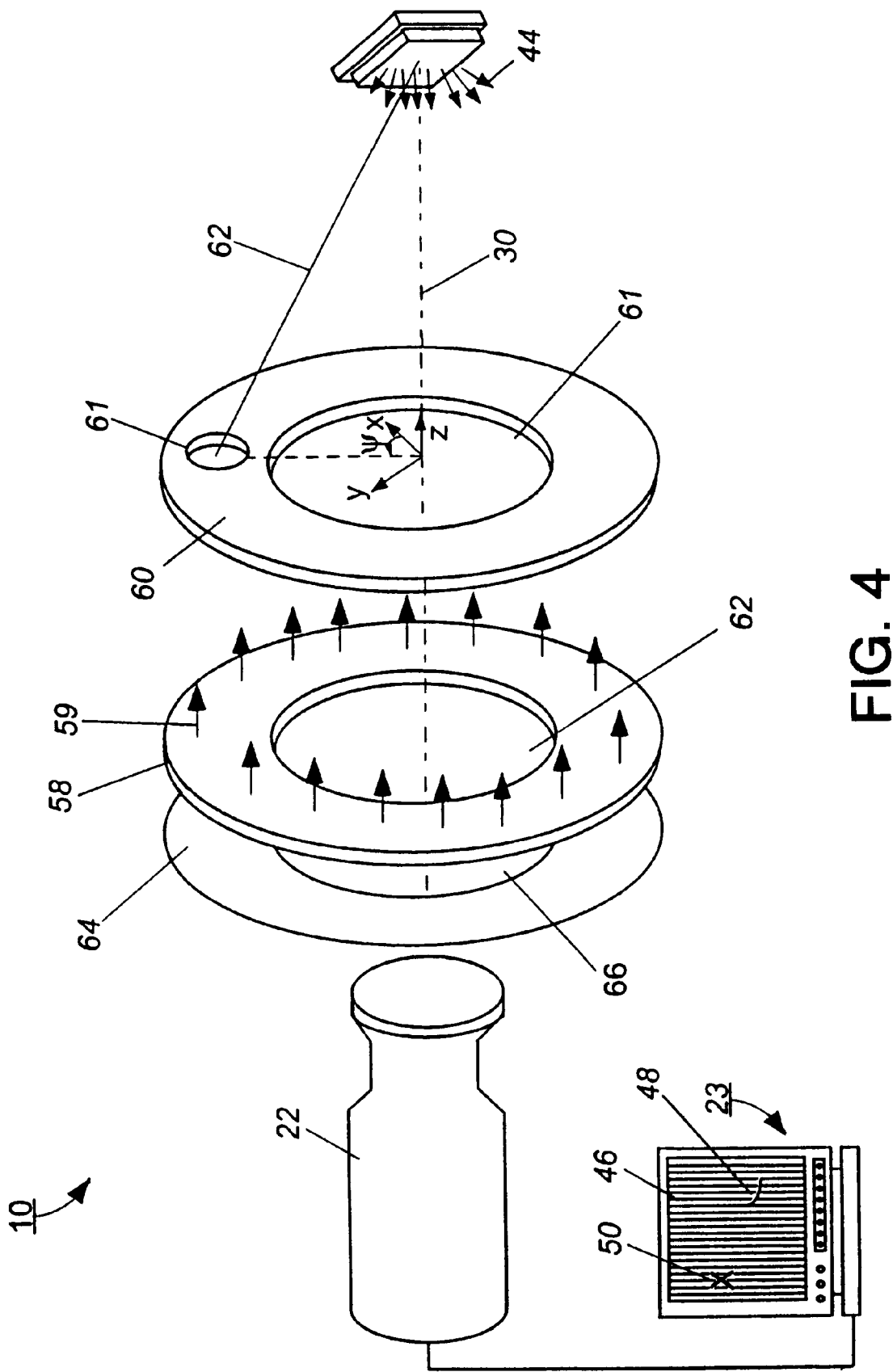
FIG. 4 is an isometric view of the inspection device in accordance with a fourth embodiment of the present invention; and, FIG. 5 is an isometric view of the inspection device in accordance with a fifth embodiment of the invention.

Referring to FIG. 4, for another embodiment of the invention, the radiating source 18 (FIG. 1) is a fixed radiating source 58 which emits electromagnetic radiation 59. A rotating plate 60 is positioned between the radiating source 58 and the cover glass 16. The rotating plate 60 is substantially opaque to electromagnetic radiation 59 and contains one or more openings 61 located at predetermined positions on the plate 60 such that a portion 62 of the infrared radiation 59 emitted from the radiating source 58 passes through the opening 61 and is incident on the cover glass 16 and substrate 14. The rotating plate 60 is rotated such that the cover glass 16 and substrate 14 is illuminated at a plurality of azimuth angles Ψ. A shield 64 is placed between the radiating source 58 and the detector 22 to shield the detector 22 from direct radiation from the radiating source 58. A shield 64 is preferably made of a material which is opaque to electromagnetic radiation 59, and includes an opening 66. The shield 64 is positioned such that the detector 22 can view the cover glass 16 and the substrate 14 through the opening 66.

Figure 5:
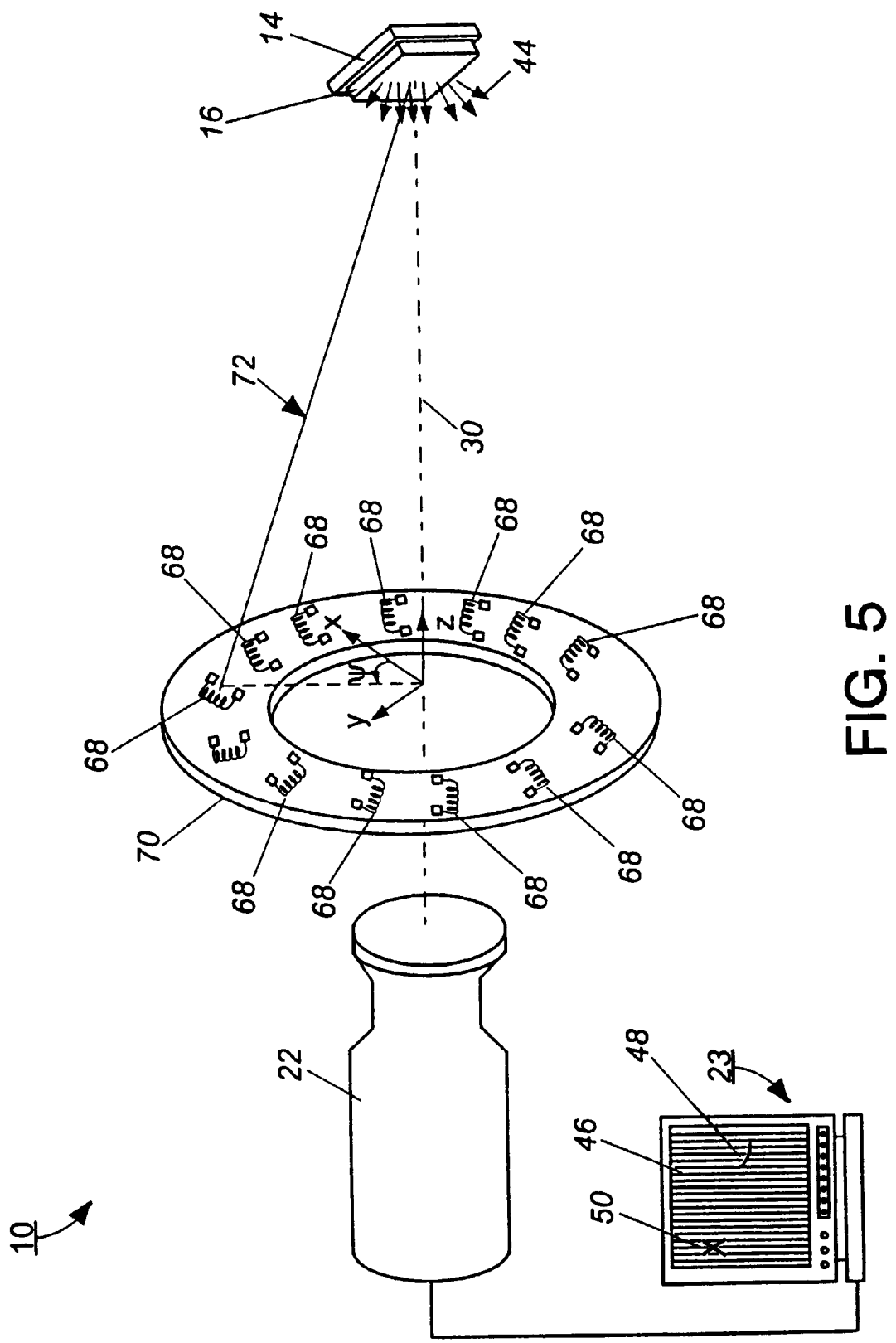

Referring to FIG. 5, for an alternative embodiment of the invention, the radiating source 18 (FIG. 1) is comprised of a plurality of radiating elements 68 each radiating element 68 located at different azimuth angles Ψ on a fixed support structure 70. Power (not shown) is provided to each radiating element 68 in a sequential fashion. Each radiating element 68 emits electromagnetic radiation 72 which is utilized to illuminate the cover glass 16 and substrate 14 at a predetermined azimuth angle Ψ. Providing power to only one radiating element 68 at a time provides the means to vary the azimuth angle Ψ at which the cover glass 16 and substrate 14 are illuminated.

Referring to FIGS. 1–5, by using electromagnetic radiation to illuminate a substrate 14 and cover glass 16 at varying azimuth angles Ψ and producing images from the collected reflected radiation as the azimuth angle Ψ is varied, the present invention provides images having indicia representative of defects in the substrate 14 and cracks in the cover glass 16 such that inspection of the substrate 14 and cover glass 16 can be conducted simply by monitoring the images, thereby eliminating the need for detailed visual inspection of the substrate 14 and cover glass 16. In addition, the present invention provides a method of inspection of a substrate 14 and cover glass 16 which detects defects in a substrate 14, detects cracks in the substrate 14 and the cover glass 16, differentiates between cracks in the substrate 14 and cracks in the cover glass 16, has a lower incidence of human error and can reduce fatigue in an inspector since rotating of an inspector's head at various angles is no longer required to provide a complete inspection of the substrate 14 and cover glass 16.

It will be appreciated by persons skilled in the art that the present invention is not limited to what has been shown and described hereinabove, nor the dimensions of sizes of the physical implementation described immediately above. The scope of invention is limited solely by the claims which follows.

What is claimed is:

1. An apparatus for detecting a defect in a substrate and a crack in a cover glass covering said substrate comprising:

a rotatable electromagnetic radiating source spaced from said cover glass and said substrate positioned to illuminate said cover glass and said substrate with electromagnetic radiation at a preselected angle of illumination and a predetermined azimuth angle, said substrate and cover glass reflecting a portion of said electromagnetic radiation, said rotatable source configured to continuously vary said azimuth angle over a 180 degree angle while maintaining substantially constant said preselected angle of illumination such that said electromagnetic radiating source illuminates said substrate and cover glass substantially continuously at said preselected angle of illumination as said azimuth angle is varied;

an electromagnetic radiation detector positioned to continually collect a portion of said reflected electromagnetic radiation as said azimuth angle is varied; and means for creating a plurality of images from said collected reflected radiation as said azimuth angle is varied, said plurality of images including indicia of said defect and said crack.

2. The apparatus as in claim 1, wherein said substrate comprises silicon solar cells, gallium arsenide solar cells, integrated circuits and energy collecting and converting devices.

3. The apparatus as in claim 1, wherein said electromagnetic radiation has a wavelength between an ultraviolet wavelength and an infrared wavelength.

4. The apparatus as in claim 1, wherein said rotatable electromagnetic radiating source comprises:

a fixed ring type radiating source; and, a plate substantially opaque to electromagnetic radiation and positioned between said radiating source and said substrate, said plate having a first opening therein such that said fixed radiating source illuminates said cover glass and substrate through said first opening at said preselected angle of illumination and said predetermined azimuth angle, said plate configured to rotate 180 degrees in azimuth and substantially continuously vary said azimuth angle over a 180 degree angle while maintaining substantially constant said preselected angle of illumination.

5. The apparatus as in claim 1, wherein said rotatable radiating source comprises a first and a second radiating element, each positioned to illuminate said cover glass and substrate at the preselected illumination angle, said first and second radiating elements positioned to illuminate said cover glass and substrate from first and second azimuth angles, respectively, said first and second azimuth angles being substantially 180 degrees apart in azimuth angle.

6. The apparatus as in claim 5, wherein said first and second radiating elements are first and second coiled wires respectively.

7. The apparatus as in claim 1, further comprising:

a shield located between said electromagnetic radiating source and said electromagnetic radiation detector and shielding said detector from said electromagnetic radiating source.

8. An apparatus for detecting a defect in a substrate and a crack in a cover glass covering said substrate, said apparatus comprising:

a first and a second electromagnetic radiating source spaced from said substrate and positioned to illuminate said cover glass and substrate with electromagnetic radiation at a first and second preselected azimuth angles, respectively, and at a preselected angle of illumination, said first and second azimuth angles being substantially 180 degrees apart, said defect and crack scattering a portion of said electromagnetic radiation;

a support structure coupled to said first and second electromagnetic radiating sources, said support structure being rotatable to continuously vary said first and second azimuth angles over a 180 degree angle such that said first and second electromagnetic radiating sources illuminate said substrate and cover glass substantially continuously at said preselected angle of illumination as said first and second azimuth angles are varied over a 180 degree azimuth angle;

a electromagnetic radiation detector positioned to continually collect portions of said reflected infrared radiation and create a plurality of images as said first and second azimuth angles are varied; and, a monitor to display said plurality of images, said plurality of images including indicia representative of said defect and said crack.

9. The apparatus as in claim 8, wherein said detector is a video camera having a first spectral response, said first and second radiating sources having second and third spectral responses respectively, said first, second and third spectral responses being substantially matched.

10. The apparatus as in claim 9, wherein said first, second and third spectral responses are from an ultraviolet to an infrared wavelength.

11. A method for detecting a defect in a substrate and a crack in a cover glass over said substrate comprising the steps of:

illuminating said substrate and cover glass with electromagnetic radiation at a preselected illumination angle and at an azimuth angle which is continuously varied over a 180 degree angle to substantially continuously illuminate said substrate and cover glass with electromagnetic radiation over an 180 degree angle in azimuth, said substrate and cover glass reflecting portions of said electromagnetic radiation;

collecting portions of said reflected electromagnetic radiation as said substrate and cover glass are illuminated at said continuously varying azimuth angle;

producing images from said collected scattered electromagnetic radiation; and, examining said images for indicia representative of said defect in said substrate and said crack in said cover glass.

12. A method for detecting a defect in a substrate including a crack in said substrate, detecting a crack in a cover glass covering said substrate and differentiating between said defect in said substrate and said crack in said cover glass, the method comprising the steps of:

illuminating said substrate and cover glass with electromagnetic radiation at a preselected illumination angle and at an azimuth angle which is continuously varied over a 180 degree angle to substantially continuously illuminate said substrate and cover glass with electromagnetic radiation over an 180 degree azimuth angle, said substrate and cover glass reflecting portions of said electromagnetic radiation;

collecting portions of said reflected electromagnetic radiation as said substrate and cover glass is illuminated at said continuously varying azimuth angle;

producing a plurality of images from said collected electromagnetic radiation;

examining said images for indicia representative of said defect in said substrate, a defect in said substrate appearing as a dark image and remaining a dark image at all azimuth angles of illumination;

examining said images for indicia representative of said crack in said cover glass, said indicia having a bright intensity when said crack is illuminated at an azimuth angle approximately normal to said glass crack, said intensity fading as said azimuth angle is varied until said intensity approximately fades completely at an azimuth angle which approximately equals said glass crack; and, differentiating said defect in said substrate from said crack in said cover glass from changes in said intensity of said indicia as said azimuth angle is varied.

* * * * *